United States Patent [19]
Ueda et al.

[11] Patent Number: 5,780,256
[45] Date of Patent: Jul. 14, 1998

[54] METHOD AND COMPOSITION FOR QUANTITATIVE DETERMINATION OF AMMONIA, α-AMINO ACID, OR α-KETO ACID

[75] Inventors: Shigeru Ueda, Tagata-gun; Mamoru Takahashi, Suntou-gun; Hideo Misaki; Shigeru Ikuta, both of Tagata-gun, all of Japan

[73] Assignee: Asahi Kasei Kogyo Kabushiki Kaisha, Osaka, Japan

[21] Appl. No.: 108,736

[22] PCT Filed: Dec. 27, 1991

[86] PCT No.: PCT/JP91/01785

§ 371 Date: Mar. 13, 1995

§ 102(e) Date: Mar. 13, 1995

[87] PCT Pub. No.: WO92/15705

PCT Pub. Date: Sep. 17, 1992

[30] Foreign Application Priority Data

Mar. 1, 1991 [JP] Japan ................................. 3-036385

[51] Int. Cl.$^6$ ...................................... C12Q 1/32
[52] U.S. Cl. .................. 435/26; 435/15; 435/25
[58] Field of Search ....................... 435/15, 25, 26

[56] References Cited

U.S. PATENT DOCUMENTS

| | | | |
|---|---|---|---|
| 3,929,581 | 12/1975 | da Fonseca-Wollheim | 195/103.5 R |
| 4,246,342 | 1/1981 | Misaki et al. | 435/25 |
| 4,666,832 | 5/1987 | Elstner et al. | 435/25 |
| 4,874,696 | 10/1989 | Payne et al. | 435/26 |
| 4,921,786 | 5/1990 | Takahashi et al. | 435/4 |
| 5,037,738 | 8/1991 | Lamos et al. | 435/12 |
| 5,356,790 | 10/1994 | Ueda et al. | 435/26 |

FOREIGN PATENT DOCUMENTS

| | | |
|---|---|---|
| 4038306 A1 | 6/1991 | Germany. |
| A-59-198995 | 11/1984 | Japan. |
| A-59-213399 | 12/1984 | Japan. |
| A-60-41500 | 3/1985 | Japan. |
| A-60-47698 | 3/1985 | Japan. |
| A-62-232397 | 10/1987 | Japan. |
| A-63-185378 | 7/1988 | Japan. |

OTHER PUBLICATIONS

Kensa Tensu Hayami Hyo, p. 289, issued by Social Insurance Research Institute, Japan, 1990.

Nippon Rinsho (Japanese Journal of Clinical Medicine), vol.47, pp. 493–498, 1989.

Proceedings of Annual Meeting of Japan Society of Clinical Chemistry, vol.27, p. 122, 1987.

Extra–edition of Journal of Medical Technology, vol.22, No.11, pp. 1322–1330 and pp. 1339–1344, Japan, 1978.

Analytical Chemistry, vol.38, pp. 188–192, Japan, 1989 partial tranlation.

Extra–edition of Japanese Journal of Clinical Medicine, vol.47, pp. 390–392, 1989.

*Primary Examiner*—Ralph Gitomer
*Attorney, Agent, or Firm*—Pennie & Edmonds LLP

[57] ABSTRACT

The present invention is directed to a method for the quantitative determination of ammonia, an α-amino acid and an α-keto acid corresponding to the α-amino acid, or a chemical substance producing any one of these compounds. The present invention is also directed to an analytical composition for use in the above method. The method of the present invention ensures rapidness and accuracy in the determination of ammonia, α-amino acids or α-keto acids, even with the use of a small quantity of a biological sample. This method is very useful in application fields, such as clinical diagnosis and food testing.

18 Claims, 8 Drawing Sheets

METHOD AND COMPOSITION FOR QUANTITATIVE DETERMINATION OF AMMONIA, α-AMINO ACID, OR α-KETO ACID

TECHNICAL FIELD

The present invention relates to a method for the quantitative determination of ammonia, an α-amino acid or an a-keto acid corresponding to the α-amino acid, or of a chemical substance producing any one of these compounds. The present invention also relates to an analytical composition for use in the above-mentioned quantitative determination.

BACKGROUND ART

Generally, in clinical diagnosis it is important to determine α-keto acids in biological samples, such as blood and urine, while in food chemistry it is important to determine α-amino acids, such as glutamic acid, contained in food. For example, organic monocarboxylic acids, such as pyruvic acid, α-ketoglutaric acid and the like, are quantitatively determined in a chemical testing of blood [Kensa Tensu Hayami Hyo, P.289, issued by Social Insurance Research Institute, Japan, 1990]. Especially, pyruvic acid, positioned at the intersections in various metabolic pathways, has been known to reflect the conditions of various diseases, and has generally been determined using lactate dehydrogenase [Nippon Rinsho (Japanese Journal of Clinical Medicine), vol.47, P.496, 1989] or pyruvate oxidase (U.S. Pat. No. 4,246,342 and Examined Japanese Patent Publication Specification No. 61-14794). The significance of L-alanine in blood as a criterion for determining the condition of a controlled diabetic has been acknowledged, and the determination of the L-alanine by the chemiluminescence method has been reported (Proceedings of Annual Meeting of Japan Society of Clinical Chemistry, vol.27, P.122, 1987).

It has also been known that the quantity of ammonia in blood is increased by a liver dysfunction or an enzyme deficiency in the urea cycle and, therefore, the determination of ammonia is useful in diagnosis of liver cirrhosis, uremia and the like. In addition, in view of the toxicity of ammonia, it is important to determine ammonia contained in food, drinking water, etc.

Conventionally, various methods are known for the determination of ammonia, α-keto acids and α-amino acids. They can be roughly classified into the microdiffusion method, ion exchange method, direct colorimetric method, enzymatic method and so on. In the microdiffusion method, an alkali is added to blood in a sealed container, and ammonia diffused from the blood is collected with an acid. In the ion exchange method, ammonium ions are adsorbed onto a cation exchange resin and then, eluted with an alkali, followed by colorimetry. In the direct colorimetric method, blood is deproteinized and then, ammonia in the blood is colorimetrically determined by indophenol reaction. These methods, however, have a drawback in that each of the methods necessarily involves two steps, i.e., a step of separating ammonia from a sample and a step of determining the separated ammonia, so that the whole procedure of each method inevitably becomes troublesome. In the meaning of the simplification of a determination process as well as the accuracy of determination, the enzymatic method is superior to the above-mentioned methods since this method utilizes a substrate specificity of an enzyme and an enzymatic reaction involved therein is conducted under ordinary physiological pH and temperature conditions, so that not only is it expected that determination results to be obtained should be closer to the real ammonia content value than those obtained by the above-mentioned other methods but the operation is also much simpler than that of the above-mentioned methods.

In the enzymatic method, ammonia, an α-keto acid or an α-amino acid is determined by measuring a change in amount of a reduced nicotinamide adenine dinucleotide (phosphate) (in terms of a change in absorbance at 340 nm with respect to the reaction mixture) in the following reversible reaction which is catalyzed by glutamate dehydrogenase (EC 1.4.1.2, EC 1.4.1.3 or EC 1.4.1.4):

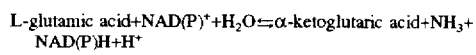

L-glutamic acid+NAD(P)$^+$+H$_2$O⇌α-ketoglutaric acid+NH$_3$+ NAD(P)H+H$^+$ (Extra-edition of Journal of Medical Technology, Vol. 22, No. 11, Japan, 1978, and Examined Japanese Patent Publication Specification No. 57-21995). This method, however, has some problems. For example, this method is difficult to use in performing accurate determinations of low levels of substances in samples. That is, this method is unsatisfactory in determining ammonia which is present in blood in a small quantity.

Still another method has also been reported for the quantitative determination of ammonia, in which a reverse reaction of the above-mentioned reaction is conducted to thereby produce glutamic acid in an equimolar amount relative to the amount of the ammonia contained in a sample. The produced glutamic acid is then reacted with glutamate oxidase to produce hydrogen peroxide in an equimolar amount relative to the amount of the produced glutamic acid, and the amount of the produced hydrogen peroxide is measured, thereby determining the ammonia from the measured amount of the hydrogen peroxide (Unexamined Japanese Patent Application Laid-Open Specification No. 60-41500). However, this method cannot provide an essential solution of the problems accompanying the prior art.

On the other hand, there is a further report regarding an enzymatic method for the quantitative determination of ammonia, in which an enzymatic cycling reaction is utilized (Unexamined Japanese Patent Application Laid-Open specification No.62-232397). In this method, two types of enzymes, i.e., glutamate dehydrogenase and glutamate oxidase are used to form the following enzymatic cycling reaction:

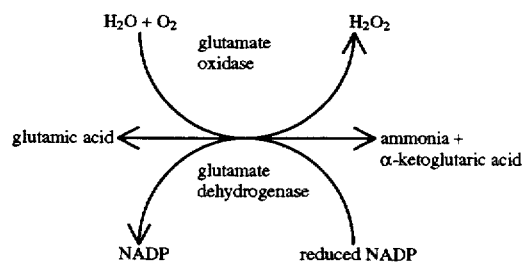

wherein NADP represents nicotinamide adenine dinucleotide phosphate.

In this method, detection is made with respect to the amount of the produced hydrogen peroxide or the amount of the consumed, reduced nicotinamide adenine dinucleotide phosphate, which reflects the amount of the ammonia contained in the starting sample. However, this method has a defect in that substrates for glutamate oxidase include not only glutamic acid, but also glutamine and aspartic acid, so that the accuracy of the determination is adversely affected when a biological sample is subjected to testing (Analytical Chemistry, Vol. 38, P188–192, Japan, 1989).

There have also been reported further enzymatic methods, that is, a method employing carbamate kinase (EC 2.7.2.2) |Unexamined Japanese Patent Application Laid-Open Specification No.59-213399| and a method employing carbamoyl-phosphate synthase (EC 6.3.4.16) |Unexamined Japanese Patent Application Laid-Open Specification No. 60-47698|. Each of these methods can be used as a highly sensitive method for the quantitative determination of ammonia. However, these methods are disadvantageous in that ADP (adenosine 5'-diphosphate) produced by a first reaction catalyzed by either of the above-mentioned enzymes can be detected only by linking the ADP to another enzymatic reaction system, so that the methods inevitably become complicated. Still a further highly sensitive method has been known for the quantitative determination of ammonia employing NAD (nicotinamide adenine dinucleotide) synthase (Unexamined Japanese Patent Application Laid-Open Specification Nos. 59-198995 and 63-185378) in which NAD produced by the above-mentioned synthase is linked to an NAD cycling reaction. This method is also disadvantageously cumbersome.

Though various types of methods for the quantitative determination of ammonia, an α-keto acid and an amino acid have been reported as described above, none of them is really suitable as a highly sensitive method for quantitative determinations except for the above-mentioned enzymatic cycling reaction employing glutamate dehydrogenase and glutamate oxidase. Even this enzymatic reaction, however, has not been widely adopted because the enzyme employed reacts with not only a target chemical substance but also coexisting non-target chemical substances in a biological sample, so that the selective, quantitative determination of the target chemical substance cannot be effectively achieved.

Among the quantitative determinations of ammonia, an α-amino acid and an α-keto acid, the quantitative determination of ammonia is especially important for the following reasons: the determination of ammonia is not only useful for determining ammonia itself, but also for determining a chemical substance other than ammonia, which participates in a reaction system producing ammonia, e.g., for determining urea in the reaction system: urea+$H_2O$→$2NH_3$+$CO_2$, which is catalyzed by urease, or for measuring the activity of the enzyme catalyzing such a reaction system.

Further, it should be noted that when the amount of a test sample itself or a target chemical substance is very small, it is desirable for a highly sensitive determination method to be available. In fact, a highly sensitive method has long been desired for the accurate, quantitative determination of ammonia since the ordinary concentration of ammonia in blood is low and widely varies depending on the type of a determination method used |e.g., the following variation has been reported with respect to the determination of a single type sample: 70–190 μg/dl by the microdiffuison method, 100–150 μg/dl by the direct colorimetric method, 20–70 μg/dl by the ion exchange method, and 12–66 μg/dl by the enzymatic method (Extra-edition of Japanese Journal of Clinical Medicine, vol. 47, P.390, 1989)|.

In the above context, the present inventors have made extensive and intensive studies with a view toward solving the above-mentioned problems accompanying the conventional methods for the quantitative determination of chemical substances in biological samples. As a result, they have found that in the reversible enzymatic reaction (producing an α-keto acid and ammonia from an α-amino acid and water) which is catalyzed by an amino acid dehydrogenase, a cycling reaction in which the following two types of coenzymes are simultaneously used: (i) a first coenzyme selected from the group consisting of thionicotinamide adenine dinucleotide or its analogue (thio-NAD compound) and thionicotiamide adenine dinucleotide phosphate or its analogue (thio-NADP compound) and (ii) a second coenzyme selected from the group consisting of nicotiamide adenine dinucleotide or its analogue (NAD compound) and nicotiamide adenine dinucleotide phosphate or its analogue (NADP compound), can be advantageously, effectively utilized for the quantitative determination of ammonia, an α-amino acid and an α-keto acid corresponding to the α-amino acid in a biological sample. That is, the target chemical substance selected from the group consisting of ammonia, an α-amino acid and an α-keto acid corresponding to the α-amino acid can be quantitatively determined by measuring a change in amount of $A_2$ or $B_1$, which is caused for a predetermined period of time during the cycling reaction represented by the following formula:

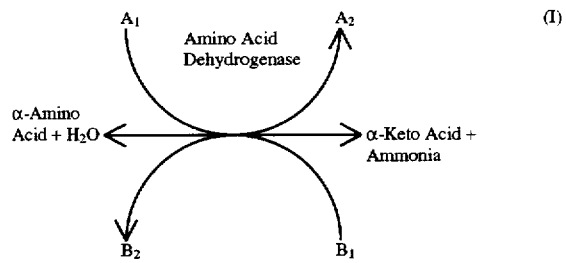

(I)

wherein $A_1$ is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$. Further, the present inventors have also found that the change in amount of coenzyme $A_2$ or $B_1$ can be easily measured in terms of the change in absorbance at a wavelength specific for coenzyme $A_2$ or $B_1$ with respect to the reaction mixture (actually, in terms of the difference in absorbance at a specific wavelength, which is observed with respect to the reaction mixture as between predetermined two time points during the above-mentioned cycling reaction) because coenzymes $A_2$ and $B_1$ are different in absorption maximum from each other (a reduced thio-NAD compound and a reduced thio-NADP compound exhibit an absorption maximum at about 400 nm, and a reduced NAD compound and a reduced NADP compound exhibit an absorption maximum at about 340 nm). Thus, a highly sensitive method for the quantitative determination of ammonia, an α-amino acid or an α-keto acid corresponding to the amino acid, which can be simply, efficiently carried out, has been realized. Based upon the above findings, the present invention has been completed.

DISCLOSURE OF THE INVENTION

Figure 1:
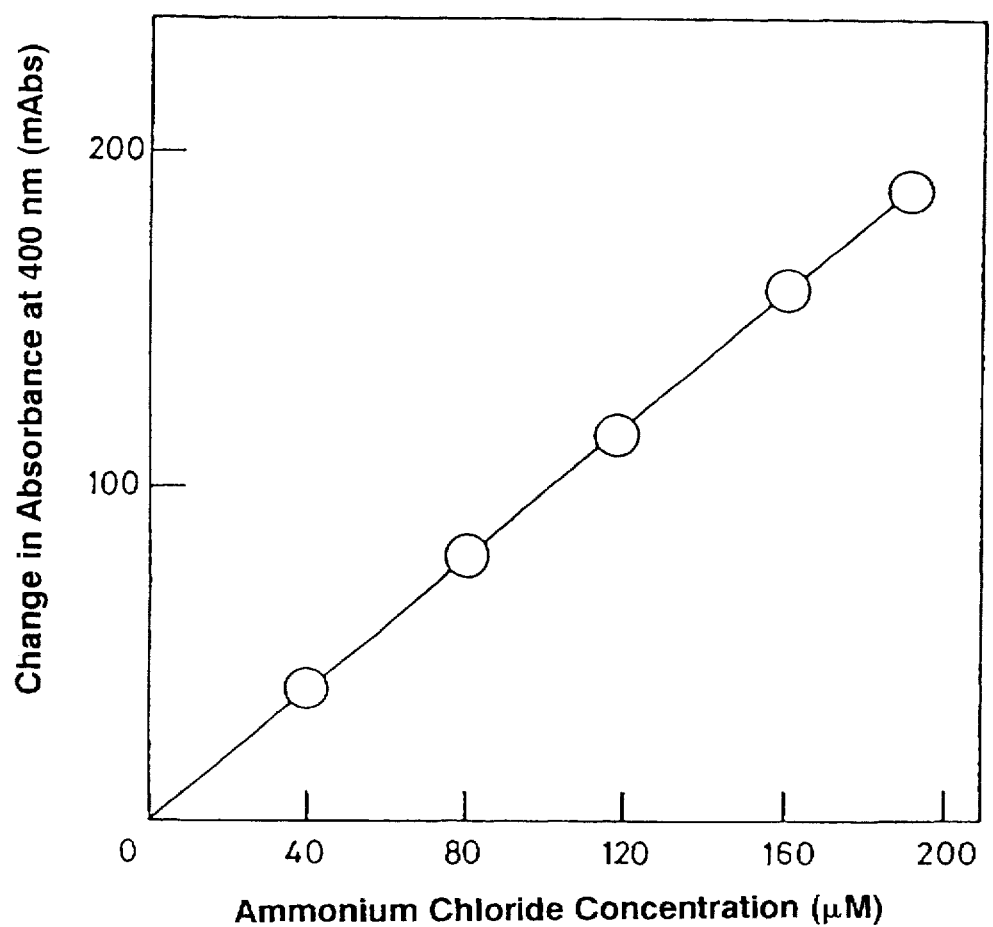
FIG. 1 is a graph showing the results of the rate assay of ammonium chloride at a wavelength of 400 nm conducted in Example 1.

According to the present invention, there is provided a method for the quantitative determination of a chemical substance selected from the group consisting of ammonia, an α-amino acid and an α-keto acid corresponding to the α-amino acid, which comprises:

reacting a biological sample containing a target chemical substance selected from the group consisting of ammonia, an α-amino acid and an α-keto acid corresponding to the α-amino acid, with a reagent comprising:

(1) an amino acid dehydrogenase which catalyzes the reversible reaction of an α-amino acid with water, the reaction producing ammonia and an α-keto acid corresponding to the α-amino acid, in the presence of (i) a first coenzyme selected from the group consisting of thionicotinamide adenine dinucleotide phosphate or its analogue (thio-NADP compound) and thionicotinamide adenine dinucleotide or its analogue (thio-NAD compound) and (ii) a second coenzyme selected from the group consisting of nicotinamide adenine dinucleotide phosphate or its analogue (NADP compound) and nicotinamide adenine dinucleotide or its analogue (NAD compound);

(2) $A_1$ (defined hereinbelow);

(3) $B_1$ (defined hereinbelow); and (4) optionally a non-target chemical substance participating in the following cycling reaction (I):

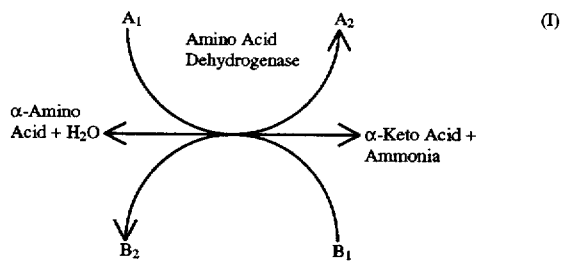

wherein $A_1$, is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$;

thereby effecting the cycling reaction (I); and measuring a change in amount of $A_2$ or $B_1$, which is caused for a predetermined period of time during the reaction (I).

In another aspect of the present invention, there is provided an analytical composition for use in the quantitative determination of a chemical substance selected from the group consisting of ammonia, an α-amino acid and an α-keto acid corresponding to the α-amino acid, which composition comprises components (1), (2), (3) and (4) as defined above.

The amino acid dehydrogenase to be used in the method of the present invention is defined as a dehydrogenase which catalyzes the reversible reaction of an α-amino acid with water, which reaction produces ammonia and an α-keto acid corresponding to the α-amino acid, in the presence of (i) a first coenzyme selected from the group consisting of a thio-NADP compound and a thio-NAD compound and (ii) a second coenzyme selected from an NADP compound and an NAD compound. A typical example of the above-mentioned reversible reaction is represented by the following formula:

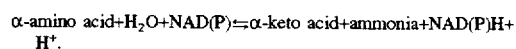

Such an amino acid dehydrogenase is present widely in living bodies, plants, bacteria and the like. Specific examples of amino acid dehydrogenases to be used in combination with a (thio)NAD compound as a coenzyme include: alanine dehydrogenase (EC 1.4.1.1) derived from *Bacillus subtilis*, *Bacillus sphaericus* and the like; glutamate dehydrogenase (EC 1.4.1.2) derived from the root of a pea, the leaf of a corn, the cotyledon of a soybean, *Micrococcus aerogenes* and the like; a common amino acid dehydrogenase, e.g., L-amino acid dehydrogenase (EC 1.4.1.5) derived from anaerobic bacteria, such as *Clostridium sporogenes*, *Clostridium saccharobutyricum*; serine dehydrogenase (EC 1.4.1.7) derived from the cotyledon of a soybean, wheat, the bud of a pea and the like; leucine dehydrogenase (EC 1.4.1.9) derived from *Bacillus cereus*, *Bacillus subtilis* SJ-2 and the like; glycine dehydrogenase (EC 1.4.1.10) derived from *Mycobacterium tuberculosis*, *Myxococcus xanthus* and the like; and L-erythro-3,5-diaminohexanoate dehydrogenase (EC 1.4.1.11) derived from *Clostridium* SB4, *Clostridium sticklandii* and the like. As examples of amino acid dehydrogenases to be used in combination with a (thio)NADP compound as a coenzyme, there can be mentioned glutamate dehydrogenase (EC 1.4.1.4) derived from yeast, *E. coli*, chlorella and the like; and valine dehydrogenase (EC 1.4.1.8) derived from the bud of a pea. As examples of amino acid dehydrogenases to be used in combination with either a (thio)NAD compound or a (thio)NADP compound as a coenzyme, there can be mentioned glutamate dehydrogenase (EC 1.4.1.3) derived from bovine liver, avian liver, *Bacillus subtilis* and the like, among which the amino acid dehydrogenases derived from animal tissues, e.g., bovine liver, are allosteric enzymes which are inhibited by GTP but activated by ADP.

With respect to glutamate dehydrogenase (EC 1.4.1.3) derived from bovine liver (which is sold by Boehringer Co., Germany and Oriental Yeast Industries Co., Ltd., Japan), when the activity exerted with use of NAD is taken as 100%, the relative activities exerted with uses of thio-NAD, NADP and thio-NADP are 40.0%, 38.9% and 14.8%, respectively (Biochem. J., 191, 299–304, 1980). With respect to glutamate dehydrogenase (EC 1.4.1.4) (derived from *proteus sp.* and sold by Toyobo Co., Japan), when the activity exerted with use of NADP is taken as 100%, the relative activity exerted with use of thio-NADP is about 15%. Other amino acid dehydrogenases of other origins also can be used in appropriate systems.

With respect to the reactivity of amino acid dehydrogenases to coenzymes, i.e., an NAD(P) compound and a thio-NAD(P) compound, there is no particular limitation as long as the amino acid dehydrogenase employed catalyzes the reversible reaction of an α-amino acid with water with the aid of the coenzymes. The reactivity can be confirmed using these coenzymes and α-amino acids as substrates as well as the amino acid dehydrogenases.

In the present invention, coenzymes $A_1$ and $B_2$ are appropriately selected from the group consisting of a thio-NADP compound, a thio-NAD compound, an NADP compound and an NAD compound in accordance with the designed reaction scheme. Examples of thio-NADP compounds and thio-NAD compounds include thionicotinamide adenine dinucleotide phosphate (thio-NADP) and thionicotinamide hypoxanthine dinucleotide phosphate; and thionicotinamide adenine dinucleotide (thio-NAD) and thionicotinamide hypoxanthine dinucleotide. Examples of NADP compounds and NAD compounds include nicotinamide adenine dinucleotide phosphate (NADP), acetylpyridine adenine dinucleotide phosphate (acetyl NADP), acetylpyridine hypoxanthine dinucleotide phosphate, nicotinamide hypoxanthine dinucleotide phosphate (deamino NADP); and nicotinamide adenine dinucleotide (NAD), acetylpyridine adenine dinucleotide (acetyl NAD), acetylpyridine hypoxanthine dinucleotide and nicotinamide hypoxanthine dinucleotide (deamino NAD). Hereinafter, reduced types of these coenzymes are referred to, for example, as a thio-NADPH compound, a thio-NADH compound, an NADPH compound and an NADH compound.

In the present invention, for example, when $A_1$ is a thio-NAD(P) compound, $B_1$ is an NAD(P)H compound, and when $A_1$ is an NAD(P) compound, $B_1$ is a thio-NAD(P)H compound.

When the amino acid dehydrogenase to be used is capable of reacting with only NAD type coenzymes, i.e., a thio-NAD compound and an NAD compound, appropriate NAD type coenzymes are selected from the above-mentioned thio-NAD compounds and NAD compounds. When the amino acid dehydrogenase to be used is capable of reacting with only NADP coenzymes, i.e., a thio-NADP compound and an NADP compound, appropriate NADP coenzymes are selected from the above-mentioned thio-NADP compounds and NADP compounds. When the amino acid dehydrogenase to be used is capable of reacting with either NAD type coenzymes or NADP type coenzymes, appropriate NAD type or NADP type coenzymes are selected from the above-mentioned thio-NAD compounds, thio-NADP compounds, NAD compounds and NADP compounds. In practice, an appropriate oxidized form or reduced form thereof is used in the method of the present invention.

By the method of the present invention, not only an α-amino acid but also ammonia or an α-keto acid, which is a reaction product of the amino acid dehy-drogenase-catalyzed reaction of an α-amino acid with water, can be quantitatively determined. When the quantitative determination of ammonia or an α-keto acid is intended, depending on the type of a target chemical substance, namely ammonia or an α-keto acid, an appropriate non-target chemical substance participating in the cycling reaction is added to the analysis reaction system involved in the method of the present invention. Illustratively stated, when a target chemical substance is ammonia, an α-keto acid corresponding to the amino acid dehydrogenase to be employed is added, whereas when a target chemical substance is an α-keto acid, ammonia is added.

According to the highly sensitive method of the present invention, it is possible to accurately determine ammonia; α-amino acids including L-glutamic acid, L-leucine, L-alanine, L-serine, L-valine, L-glycine and the like; or α-keto acids including pyruvic acid, α-ketoglutaric acid, hydropyruvic acid, 2-oxoisovaleric acid, oxoisocaproic acid, glyoxalic acid and the like, which are originally present in such forms in biological samples.

The method of the present invention has other utilities. That is, it is possible not only to determine a substrate in an enzymatic reaction system producing the above substances, but also measure the activity of an enzyme involved in such an enzymatic reaction system. Further, according to the highly sensitive method of the present invention, it is possible not only to determine a substrate in an enzymatic reaction system which comprises one or more reaction steps and can be linked to the enzymatic reaction system producing ammonia, an α-amino acid or an α-keto acid, but also measure the activity of an enzyme involved in the first-mentioned enzymatic reaction system. Illustrative examples of such utilities are described below.

(1) Enzymatic reaction of creatinine, catalyzed by creatinine deiminase (EC 3.5.4.21):

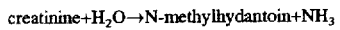

In the system involving the above reaction, by determining ammonia produced, not only can creatinine be determined, but also the activity of creatinine deiminase can be measured.

(2) Enzymatic reaction of urea, catalyzed by urease (EC 3.5.1.5):

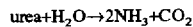

In the system involving the above reaction, by determining ammonia produced, not only can urea be determined, but also the activity of urease can be measured.

(3) Enzymatic reaction of guanine and, catalyzed by guanine deaminase (EC 3.5.4.3):

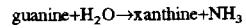

In the system involving the above reaction, by determining ammonia produced, not only can guanine be determined, but also the activity of guanine deaminase can be measured.

(4) Enzymatic reaction of adenosine, catalyzed by adenosine deaminase (EC 3.5.4.4 or EC 3.5.4.17):

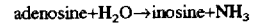

In the system involving the above reaction, by determining ammonia produced, not only can adenosine be determined, but also the activity of adenosine deaminase can be measured.

(5) Enzymatic reaction of asparagine, catalyzed by asparaginase (EC 3.5.1.1):

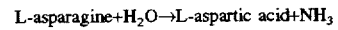

In the system involving the above reaction, by determining ammonia or L-aspartic acid produced, not only can L-asparagine be determined, but also the activity of asparaginase can be measured.

(6) Enzymatic reaction of ADP, catalyzed by ammonia kinase (EC 2.7.3.8) (the ADP is produced by the pre-enzymatic reaction catalyzed by a certain kinase, in which a substrate for the kinase is reacted with ATP):

ADP+phosphoramide→ATP+NH₃

In the system involving the above reaction, by determining ammonia produced, not only can ADP or any one component participating in the above-mentioned pre-enzymatic reaction be determined, but also the activity of ammonia kinase can be measured.

(7) Enzymatic reaction of ethanolamine, catalyzed by ethanolamine deaminase (EC 4.3.1.7):

ethanolamine→acetaldehyde+NH₃

In the system involving the above reaction, by determining ammonia produced, not only can ethanolamine be determined, but also the activity of ethanolamine deaminase can be measured.

(8) Enzymatic reaction of phosphoenolpyruvic acid and ADP, catalyzed by pyruvate kinase (EC 2.7.1.40):

phosphoenolpyruvic acid+ADP→pyruvic acid+ATP

In the system involving the above reaction, by determining pyruvic acid produced, not only can phosphoenolpyruvic acid or ADP be determined, but also the activity of pyruvate kinase can be measured.

(9) Enzymatic reaction of N-acetylneuraminic acid, catalyzed by N-acetylneuraminate aldolase (EC 4.1.3.3):

N-acetylneuraminic acid→N-acetylmannosamine+pyruvic acid

In the system involving the above reaction, by determining pyruvic acid produced, not only can N-acetylneuraminic acid be determined, but also the activity of N-acetylneuraminate aldolase can be measured.

(10) Enzymatic reaction of isocitric acid and NAD(P), catalyzed by isocitrate dehydrogenase (EC 1.1.1.41 or EC 1.1.1.42):

isocitric acid+NAD(P)→α-ketoglutaric acid+CO₂+NAD(P)H

In the system involving the above reaction, by determining α-ketoglutaric acid produced, not only can isocitrate be determined, but also the activity of isocitrate dehydrogenase can be measured.

(11) Enzymatic reaction of sarcosine, catalyzed by sarcosine dehydrogenase (EC 1.5.99.1) or sarcosine oxidase (EC 1.5.3.1), (which sarcosine is produced by the pre-enzymatic reaction of creatinine or creatine, catalyzed by creatininase or creatinase, respectively):

sarcosine+hydrogen acceptor+H₂O→glycine+formaldehyde+H₂O₂, or sarcosine+O₂+H₂O→glycine+formaldehyde+H₂O₂

In the system involving the above reaction, by determining glycine produced, not only can sarcosine or any one component participating in the above-mentioned pre-enzymatic reaction be determined, but also the activity of sarcosine dehydrogenase or sarcosine oxidase can be measured.

In the method of the present invention, component (2) (coenzyme $A_1$), component (3) (coenzyme $B_1$) and optional component (4) (non-target chemical substance participating in the cycling reaction) are used in excess amounts relative not only to the amount of a target chemical substance, but also the respective Km (Michaelis constant) values of components (1) (amino acid dehydrogenase) for components (2), (3) and (4). It is especially preferred to use components (2), (3) and (4) individually in amounts of from 20 to 10,000 moles per mole of the target chemical substance.

For example, when the target chemical substance is an α-amino acid, each of $A_1$, $B_1$ and an α-keto acid or ammonia is used in an excess amount as compared not only to the amount of the α-amino acid but also the respective Km values of an amino acid dehydrogenase for $A_1$, $B_1$ and the α-keto acid or ammonia, and such an amount is preferably from 20 to 10,000 moles per mole of the α-amino acid.

Also for example, when the target chemical substance is an α-keto acid, each of $A_1$, $B_1$, and ammonia is used in an excess amount as compared not only to the amount of the α-keto acid but also the respective Km values of an amino acid dehydrogenase for $A_1$, $B_1$ and ammonia, and such an amount is preferably from 20 to 10,000 moles per mole of the α-keto acid.

Also for example, when the target chemical substance is ammonia, each of $A_1$, $B_1$ and an α-keto acid is used in an excess amount as compared not only to the amount of the ammonia but also the respective Km values of an amino acid dehydrogenase for $A_1$, $B_1$ and the α-keto acid, and such an amount is preferably 20 to 10,000 moles per mole of the ammonia.

As mentioned above, in another aspect of the present invention, there is provided an analytical composition for use in the above-mentioned quantitative determination. In the analytical composition of the present invention, the concentration of each of component (2) ($A_1$) and component (3) ($B_1$) is 0.02 to 100 mM, preferably 0.05 to 20 mM, the concentration of ammonia or an α-keto acid which is used as optional component (4) for advancing the cycling reaction is 3 to 100 mM, preferably 5 to 50 mM, and the concentration of component (1) (amino acid dehydrogenase) is 5 to 1,000 u/ml, preferably 20 to 400 u/ml. However, an appropriate concentration of each of components (1) (2) (3) and (4) in the analytical composition is varied depending on the type of a biological sample to be tested and, if desired, these components can be used in more large amounts.

In the present invention, when $B_2$ functions also as a coenzyme for a certain dehydrogenase other than the amino acid dehydrogenase of the cycling reaction (I), which certain dehydrogenase does not react with an α-amino acid but acts to advance the reaction for converting $B_2$ to $B_1$ in cooperation with a substrate for the certain dehydrogenase, such a certain dehydrogenase (which is hereinafter frequently referred to as "second dehydrogenase") can also be additionally incorporated together with a substrate therefor (second dehydrogenase is referred to as "component (5)") into the analytical reagent for effecting the following cycling reaction (II):

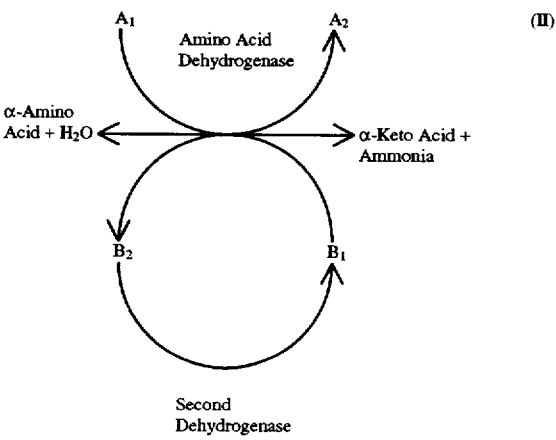

wherein $A_1$ is a thio-NADP compound, a thio-NAD compound, an NADP compound or an NAD compound; $A_2$ is a reduced product of $A_1$; $B_1$, is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$.

In the above reaction system, as the second dehydrogenase, a dehydrogenase which does substantially not react with $A_1$ but acts to advance the reaction for converting $B_2$ to $B_1$ is chosen. Alternatively, by choosing reaction conditions under which the second dehydrogenase does not react with $A_1$. The objective can be attained. For example, there can be chosen appropriate $A_1$-$B_2$ amount relationship conditions under which the second dehydrogenase does substantially not react with $A_1$. The quantitative determination of the target chemical substance participating in reaction (II), can be achieved by measuring a change in the amount of $A_2$ |which is caused for a predetermined period of time during reaction (II)|.

The second dehydrogenase can be advantageously used in order to regenerate $B_1$, so that the amount of $B_1$ to be used in the analytical reaction can be reduced. This is particularly useful when $B_1$ is an expensive compound. It is also possible to use $B_2$ alone or a mixture of $B_1$ and $B_2$ at the initiation of the reaction. For conducting reaction (II), an amount of at least one coenzyme selected from $B_1$ and $B_2$ is preferably not larger than 1/10 mole per mole of $A_1$, although the amount is not particularly limited.

In practicing the above method for quantitative determination of the present invention using a second dehydrogenase as component (5), $A_1$ is used in a concentration of 0.02 to 100 mM, preferably 0.05 to 20 mM. $B_2$ and/or $B_1$ is used in a concentration of 0.05 to 5,000 μM, preferably 5 to 500 μM. Ammonia or an α-keto acid as optional component (4) for advancing the cycling reaction (II) is used in a concentration of 3 to 100 mM, preferably 5 to 50 mM. An amino acid dehydrogenase as the first dehydrogenase is used in a concentration of 5 to 1000 u/ml, preferably 20 to 500 u/ml. The concentration of the second dehydrogenase (u/ml) can be 20 times or more the Km value (unit: mM) thereof for $B_2$, e.g., 1 to 100 u/ml. The substrate for the second dehydrogenase can be used in a stoichiometrically excess amount, for example, 0.05 to 20 mM. The amounts of the components of the reagent for the cycling reaction can be varied depending on the type of a biological sample to be tested. The amount exceeding the above can also be employed.

As examples of combinations of second dehydrogenases and substrates therefor, the following combinations can be mentioned. When $B_2$ is an NAD compound or a thio-NAD compound, there can be mentioned combinations of: alcohol dehydrogenase (EC 1.1.1.1) and ethanol; glycerol dehydrogenase (EC 1.1.1.6) derived from *E. coli* and glycerol; glycerol-3-phosphate dehydrogenase (EC 1.1.1.8) derived from rabbit muscle and L-glycerol-3-phosphate; malate dehydrogenase (EC1.1.1.37) derived from pig or bovine heart and L-malic acid; and glyceraldehyde phosphate dehydrogenase (EC1.1.1.12) derived from rabbit muscle, liver, yeast or *E. coli*, D-glyceraldehyde phosphate and phosphoric acid. When $B_2$ is an NADP compound or a thio-NADP compound, there can be mentioned combinations of: glucose-6-phosphate dehydrogenase (EC 1.1.1.49) derived from yeast and glucose-6-phosphate; isocitrate dehydrogenase (EC 1.1.1.42) derived from yeast or pig heart and iso-citric acid; glyoxylate dehydrogenase (EC 1.2.1.17) derived from *Pseudomonas oxalaticus*, CoA and glyoxylic acid; phosphogluconate dehydrogenase (EC 1.1.1.44) derived from rat liver, beer yeast or *E. coli* and 6-phospho-D-gluconic acid; glyceraldehyde phosphate dehydrogenase (EC 1.2.1.13) derived from plant chlorophyll, D-glyceraldehyde-3-phosphate and phosphoric acid; and benzaldehyde dehydrogenase (EC 1.2.1.7) derived from *Pseudomonas fluorescens* and benzaldehyde.

Furthermore, in the present invention, when $A_2$ functions also as a coenzyme for a certain dehydrogenase other than the amino acid dehydrogenase of the reaction (I) and the second dehydrogenase of the reaction (II), which certain dehydrogenase does not react with an α-amino acid but acts to advance the reaction for converting $A_2$ to $A_1$ in cooperation with a substrate for the certain dehydrogenase, such a certain dehydrogenase (which is hereinafter frequently referred to as "third dehydrogenase") can also be additionally incorporated together with a substrate therefor (third dehydrogenase is referred to also as "component (6)") into the analytical reagent for effecting the following cycling reaction (III):

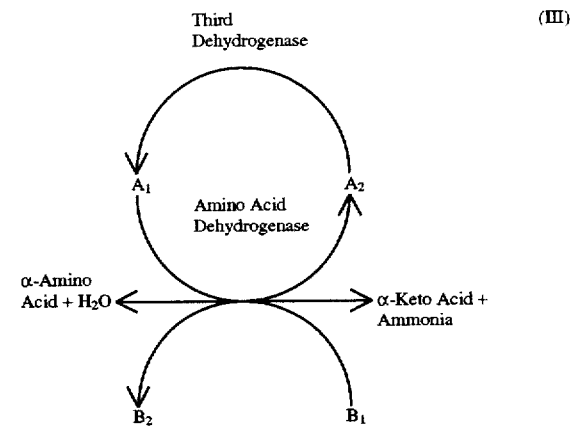

wherein $A_1$ is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$.

In the above reaction system, as the third dehydrogenase, a dehydrogenase which does substantially not react with $B_1$, but acts to advance the reaction for converting $A_2$ to $A_1$, is chosen. Alternatively, by choosing reaction conditions under which the third dehydrogenase does not react with $B_1$, the objective can be attained. For example, there can be chosen appropriate $B_1$-$A_2$ amount relationship conditions under which the third dehydrogenase does substantially not react with $B_1$. The quantitative determination of the target chemical substance participating in reaction (III), can be achieved by measuring a change in amount of $B_1$ |which is caused for a predetermined period of time during reaction (III)|.

The third dehydrogenase can be advantageously used in order to regenerate $A_1$, so that the amount of $A_1$ to be used in the analytical reaction can be reduced. This is particularly useful when $A_1$ is an expensive compound. It is also possible to use $A_2$ alone or a mixture of $A_1$ and $A_2$, at the initiation of the reaction. For conducting reaction (III), an amount of at least one coenzyme selected from $A_1$ and $A_2$ is preferably not larger than 1/10 mole per mole of $B_1$, although the amount is not particularly limited.

In practicing the above method for quantitative determination of the present invention using a third dehydrogenase as component (6), $B_1$ is used in a concentration of 0.02 to 100 mM, preferably 0.05 to 20 mM. $A_2$ and/or $A_1$ is used in a concentraion of 0.05 to 5.000 μM, preferably 5 to 500 μM. Ammonia or an α-keto acid as optional component (4) for advancing the cycling reaction (III) is used in a concentration of 3 to 100 mM, preferably 5 to 50 mM. An amino acid dehydrogenase as the first dehydrogenase is used in a concentration of 5 to 1000 u/ml, preferably 20 to 500 u/ml. The concentration of the third dehydrogenase (u/ml) can be 20 times or more the Km value (unit: mM) thereof for $A_2$, e.g., 1 to 100 u/ml. The substrate for the third dehydrogenase can be used in a stoichiometrically excess amount, for example, 0.05 to 20 mM. The amounts of the components of the reagent for the cycling reaction can be varied depending on the type of a biological sample to be tested. The amounts exceeding the above can also be employed.

As Examples of combinations of third dehydrogenases and substrates therefor, the following combinations can be mentioned. When $A_1$ is an NAD compound or a thio-NAD compound, there can be mentioned combinations of: alcohol dehydrogenase (EC 1.1.1.1) and acetaldehyde; glycerol dehydrogenase (EC 1.1.1.6) derived from *E. coli* and dihydroxyacetone; glycerol-3-phosphate dehydrogenase (EC 1.1.1.8) derived from rabbit muscle and dihydroxyacetone phosphate; malate dehydrogenase (EC 1.1.1.37) derived from pig or bovine heart and oxaloacetic acid; and glyceraldehyde phosphate dehydrogenase (EC 1.1.1.12) derived from rabbit muscle, liver, yeast or *E. coli* and 1,3-diphospho-D-glycerate. When $A_1$ is an NADP compound or a thio-NADP compound, there can be mentioned combinations of: glucose-6-phosphate dehydrogenase (EC 1.1.1.49) derived from yeast and gluconolactone-6-phosphate; and glyceraldehyde phosphate dehydrogenase (EC 1.2.1.13) derived from plant chlorophyll and 1,3-diphospho-D-glycerate.

In practicing the method for the quantitative determination of ammonia, an α-amino acid or an α-keto acid corresponding to the α-amino acid in a biological sample by using the analytical composition of the present invention, 0.001 to 0.5 ml of the biological sample can be added to an aqueous composition containing the above-defined components (1) to (4), (1) to (5), or (1) to (4) and (6), and the resultant solution is reacted at about 37° C. Then, a change in absorbance at a wavelength specific for coenzyme $A_2$ or $B_1$ is measured, which is observed with respect to the reaction mixture as between predetermined two time points during the reaction (e.g., between 3 and 4 minutes after the start of the reaction, or between 3 and 8 minutes after the start of the reaction). The period between such two time points during the reaction can be varied in the range from several minutes to several tens of minutes, depending on the type of a biological sample and the type of a target chemical substance contained therein. For example, when $A_2$ is a thio-NADH compound and $B_1$ is an NADH compound, either the produced $A_2$ is determined in terms of the change in absorbance at 400 nm, or the consumed $B_1$ is determined in terms of the change in absorbance at 340 nm. The thus obtained change in absorbance reflecting the amount of the target chemical substance is applied to a calibration curve which has been prepared with respect to standard samples containing the target chemical substance in different concentrations, to thereby determine the amount of the target chemical substance.

By the method of the present invention, it becomes possible to realize a real-time quantitative determination of a target chemical substance in a biological sample.

Furthermore, the method of the present invention is so designed that a target chemical substance (e.g., ammonia, an α-amino acid or an α-keto acid corresponding to the α-amino acid) itself participates in the enzymatic cycling reaction. Therefore, the determination of the target chemical substance of the method of the present invention is less influenced by other compounds present in the sample, so that the desired determination can be easily, simply done by rate assay without requiring any blank assay of the sample.

With respect to the determination of $A_2$ or $B_1$, other known methods can be used instead of the measurement of absorbances described above.

Best Mode for Carrying Out the Invention

Hereinbelow, the present invention will be illustrated with reference to the following examples, which however should not be construed as limiting the present invention.

Example 1 Quantitative Determination of Ammonia

| Reagent | | |
|---|---|---|
| 40 mM | Tris-HCl buffer (pH 8.9) | |
| 3 mM | ADP (manufactured by Oriental Yeast Co., Ltd., Japan) | |
| 2 mM | thio-NAD (manufactured by Sigma Co., Ltd., U.S.A.) | |
| 0.2 mM | reduced NAD (manufactured by Oriental Yeast Co., Ltd., Japan) | |
| 5 mM | α-ketoglutaric acid (manufactured by Wako Pure Chemical Industries, Ltd., Japan) | |
| 3 mM | EDTA | |
| 128 u/ml | glutamate dehydrogenase (derived from bovine liver and manufactured by Boehringer Co., Germany) | |

Procedure 1 ml of the above reagent was placed in each of six cuvettes. To the respective cuvettes were individually added 50 μl each of six types of aqueous ammonium chloride solutions respectively having concentrations of 0, 40, 80, 120, 160 and 200 μM. The resultant mixtures in the respective cuvettes were individually allowed to react at 37° C. With respect to each of respective samples taken from the reaction mixtures in the six cuvettes, absorbances at 400 nm were measured 2 minutes and 4 minutes after the start of the reaction, and a change in absorbance as between the above two time points was calculated with respect to each of the samples. Results are shown in FIG. 1, which demonstrates the presence of good linearity in the relationship between the change (difference) in absorbance (with respect to the reaction mixture as between 2 and 4 minutes after the start of the reaction) and the ammonium chloride concentration.

Example 2 Quantitative Determination of Ammonia

| Reagent | | |
|---|---|---|
| 100 mM | Tris-HCl buffer (pH 9.5) | |
| 1 mM | thio-NADP (manufactured by Sigma Co., Ltd., U.S.A.) | |
| 0.2 mM | reduced NADP (manufactured by Oriental Yeast Co., Ltd., Japan) | |
| 10 mM | α-ketoglutaric acid (manufactured by Wako Pure Chemical Industries, Ltd., Japan) | |
| 5 mM | EDTA | |
| 250 u/ml | glutamate dehydrogenase (derived from Proteus sp. and manufactured by Toyobo Co., Ltd., Japan) | |

Figure 2:
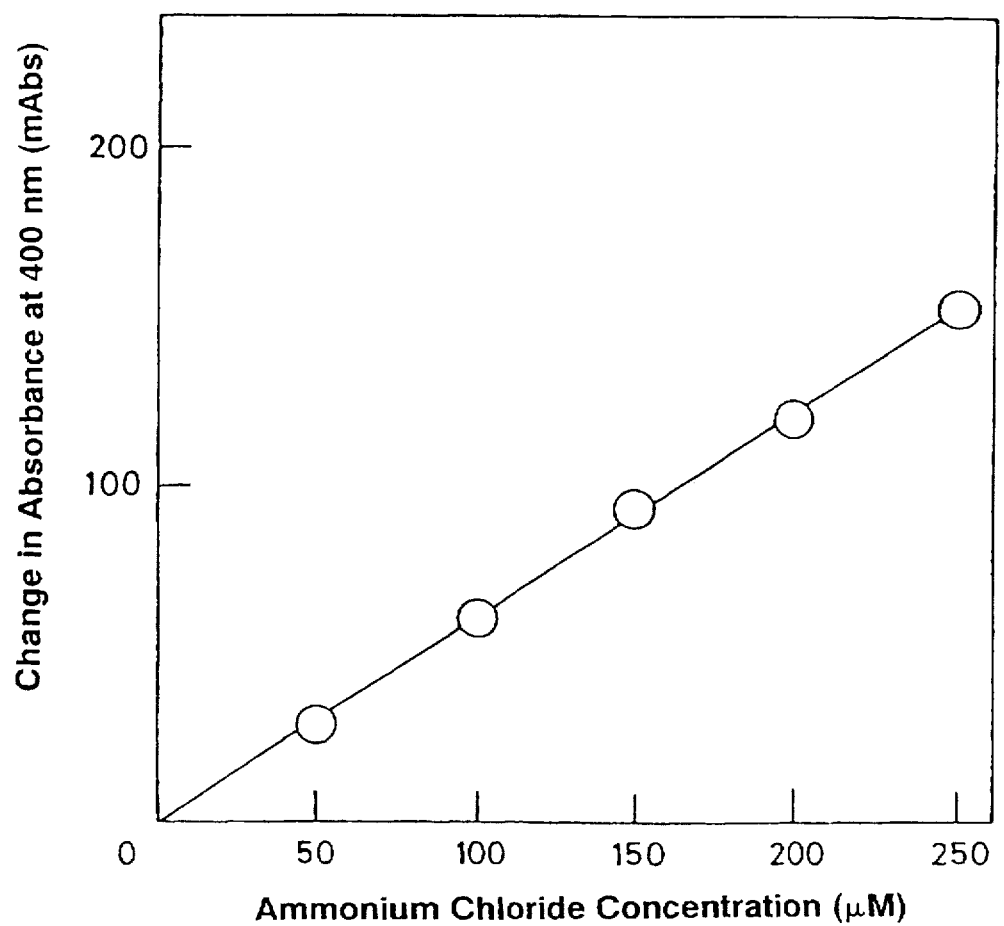
FIG. 2 is a graph showing the results of the rate assay of ammonium chloride at a wavelength of 400 nm conducted in Example 2.

Procedure 1 ml of the above reagent was placed in each of six cuvettes. To the respective cuvettes were individually 50 μl each of six types of aqueous ammonium chloride solutions respectively having concentrations of 0, 50, 100, 150, 200 and 250 μM. The resultant mixtures in the respective cuvettes were individually allowed to react at 37° C. With respect to each of respective samples taken from the reaction mixtures in the six cuvettes, absorbances at 400 nm were measured 2 minutes and 4 minutes after the start of the reaction, and a change in absorbance as between the above two time points was calculated with respect to each of the samples. Results are shown in FIG. 2, which demonstrates the presence of good linearity in the relationship between the change (difference) in absorbance (with respect to the reaction mixture, as between 3 and 4 minutes after the start of the reaction) and the ammonium chloride concentration.

Example 3 Quantitative Determination of L-glutamic Acid

| | Reagent |
|---|---|
| 100 mM | Tris-HCl buffer (pH 9.5) |
| 1 mM | thio-NADP (manufactured by Sigma Co., Ltd., U.S.A.) |
| 0.2 mM | reduced NADP (manufactured by Oriental Yeast Co., Ltd., Japan) |
| 5 mM | ammonium chloride (manufactured by Wako Pure Chemical Industries, Ltd., Japan) |
| 5 mM | EDTA |
| 250 u/ml | glutamate dehydrogenase (derived from Proteus sp. and manufactured by Toyobo Co., Ltd., Japan) |

Figure 3:
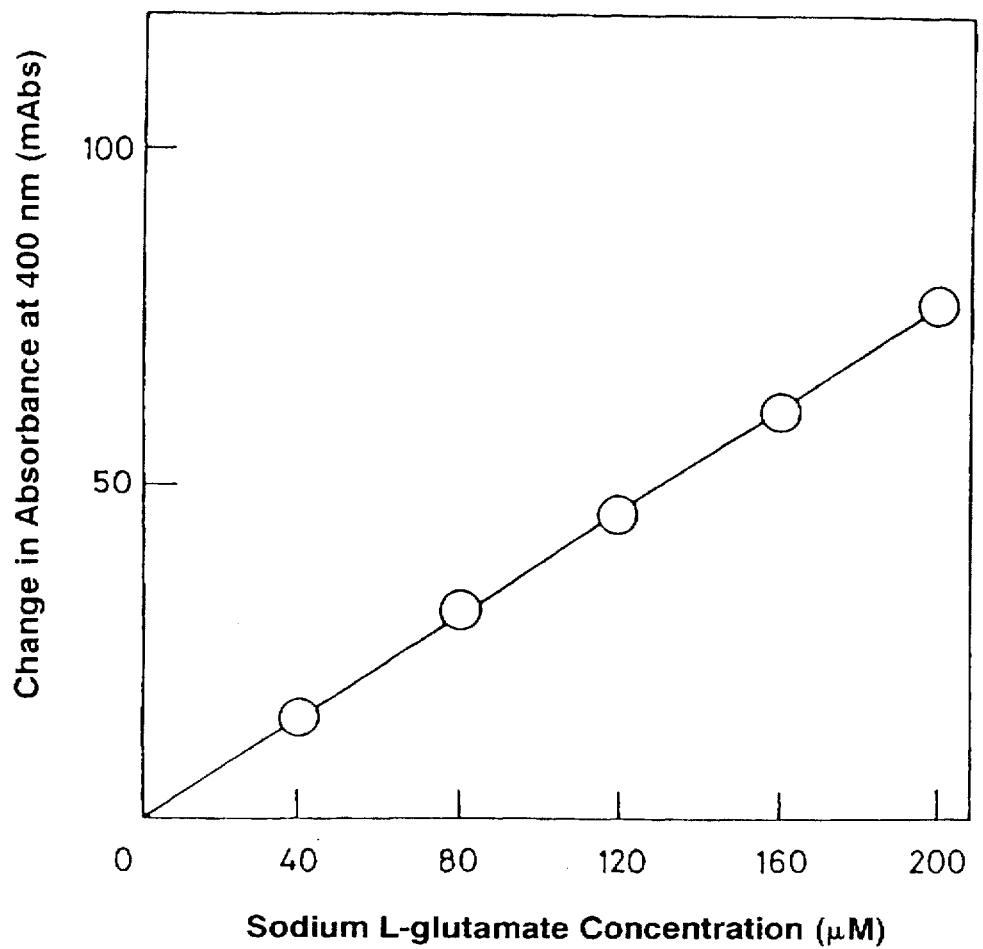
FIG. 3 is a graph showing the results of the rate assay of sodium L-glutamate at a wavelength of 400 nm conducted in Example 3.

Procedure 1 ml of the above reagent was placed in each of six cuvettes. To the respective cuvettes were individually added 50 μl each of six types of aqueous sodium L-glutamate solutions respectively having concentrations of 0, 40, 80, 120, 160 and 200 μM. The resultant mixtures in the respective cuvettes were individually allowed to react at 37° C. With respect to each of respective samples taken from the reaction mixtures in the six cuvettes, absorbances at 400 nm were measured 3 minutes and 4 minutes after the start of the reaction, and a change in absorbance as between the above two time points was calculated with respect to each of the samples. Results are shown in FIG. 3, which demonstrates the presence of good linearity in the relationship between the change (difference) in absorbance (with respect to the reaction mixture, as between 3 and 4 minutes after the start of the reaction) and the sodium L-glutamate concentration.

Example 4 Quantitative Determination of Creatinine

| | Reagent |
|---|---|
| 250 mM | Tris-HCl buffer (pH 9.5) |
| 2 mM | thio-NADP (manufactured by Sigma Co., Ltd., U.S.A.) |
| 0.2 mM | reduced NADP (manufactured by Oriental Yeast Co., Ltd., Japan) |
| 10 mM | α-ketoglutaric acid (manufactured by Wako Pure Chemical Industries, Ltd., Japan) |
| 5 mM | EDTA |
| 20 u/ml | creatinine deiminase (derived from microorganism and manufactured by Toyobo Co., Ltd., Japan) |
| 250 u/ml | glutamate dehydrogenase (derived from Proteus sp. and manufactured by Toyobo Co., Ltd., Japan) |

Figure 4:
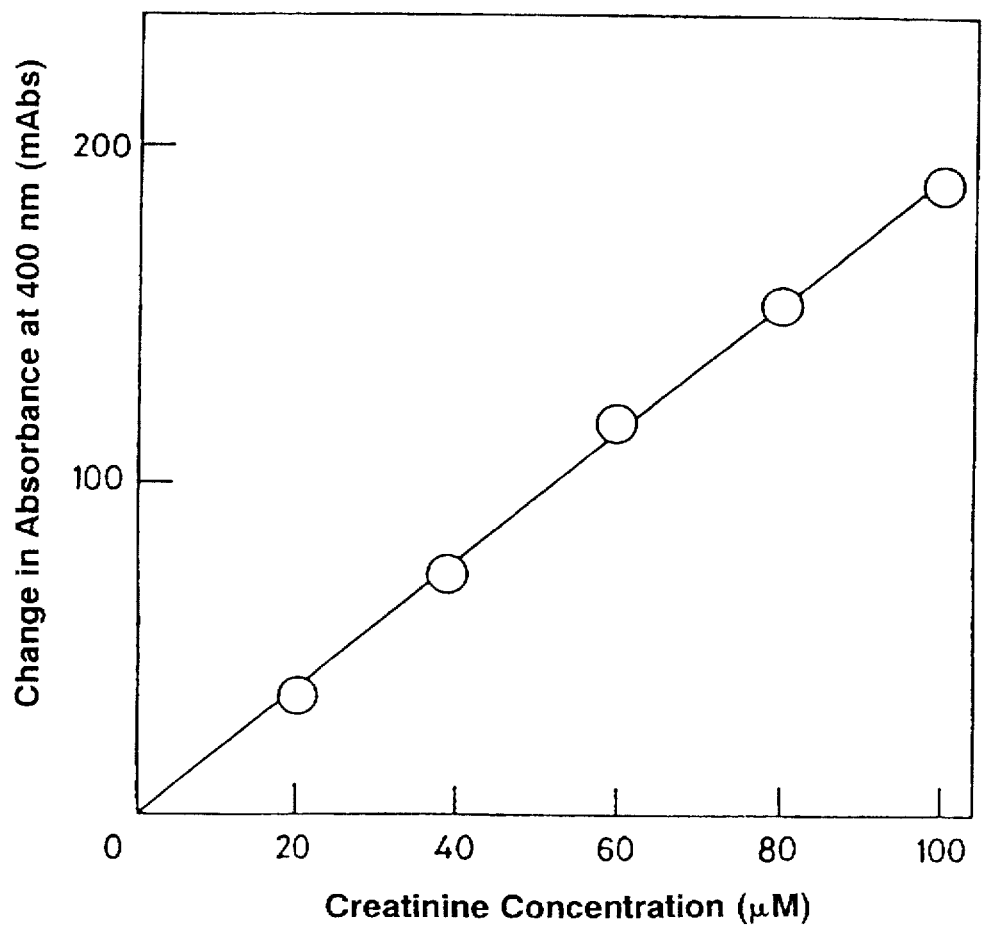
FIG. 4 is a graph showing the results of the rate assay of creatinine at a wavelength of 400 nm conducted in Example 4.

Procedure 1 ml of the above reagent was placed in each of six cuvettes. To the respective cuvettes were individually added 50 μl each of six types of aqueous creatinine (manufactured by Wako Pure Chemical Industries, Ltd., Japan) solutions respectively having concentrations of 0, 20, 40, 60, 80 and 100 μM. The resultant mixtures in the respective cuvettes were individually allowed to react at 37° C. With respect to each of respective samples taken from the reaction mixtures in the six cuvettes, absorbances at 400 nm were measured 3 minutes and 8 minutes after the start of the reaction, and a change in absorbance as between the above two time points was calculated with respect to each of the samples. Results are shown in FIG. 4, which demonstrates the presence of good linearity in the relationship between the change (difference) in absorbance (with respect to the reaction mixture, as between 3 and 8 minutes after the start of the reaction) and the creatinine concentration.

Example 5 Quantitative Determination of L-leucine

| | Reagent |
|---|---|
| 40 mM | Tris-HCl buffer (pH 8.9) |
| 2 mM | thio-NAD (manufactured by Sigma Co., Ltd., U.S.A.) |
| 0.25 mM | reduced NAD (manufactured by Oriental Yeast Co., Ltd., Japan) |
| 100 mM | ammonium chloride (manufactured by Wako Pure Chemical Industries, Ltd., Japan) |
| 100 u/ml | leucine dehydrogenase (EC 1.4.1.9, derived from Bacillus sp. and manufactured by Toyobo Co., Ltd., Japan) |

Figure 5:
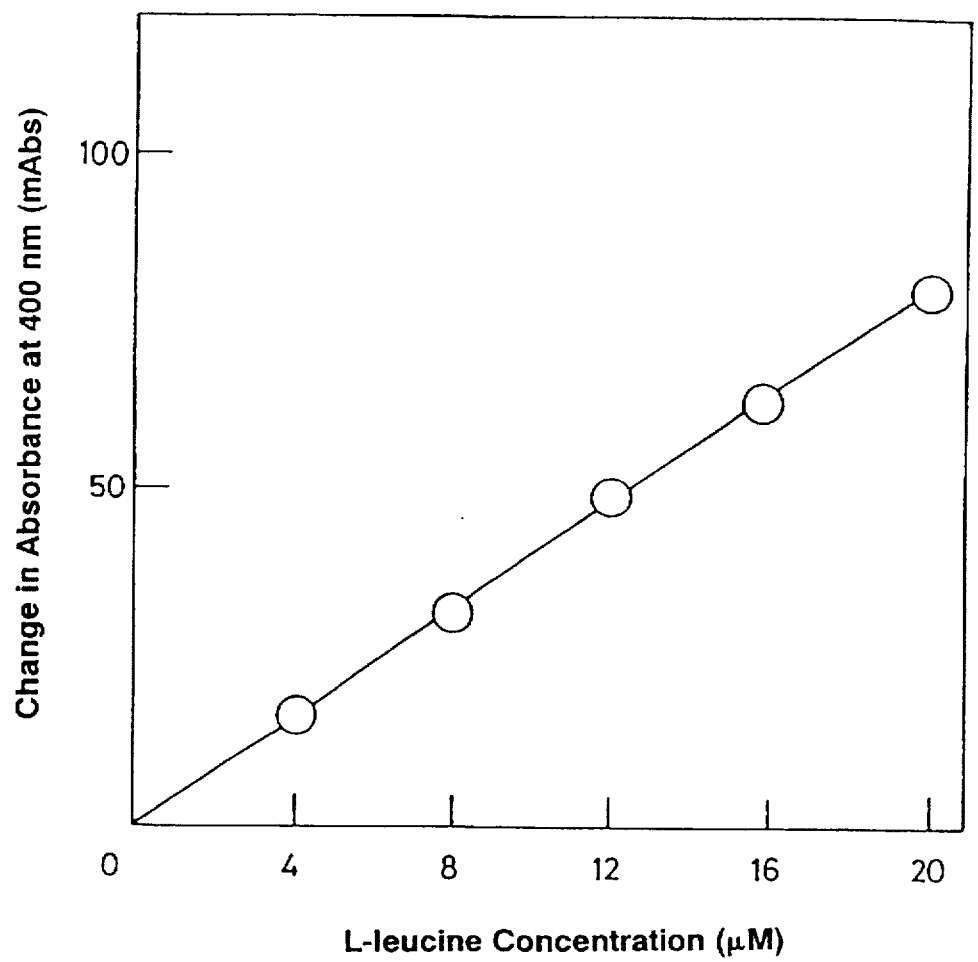
FIG. 5 is a graph showing the results of the rate assay of L-leucine at a wavelength of 400 nm conducted in Example 5.

Procedure 1 ml of the above reagent was placed in each of six cuvettes. To the respective cuvettes were individually added 50 μl each of six types of aqueous L-leucine solutions respectively having concentrations of 0, 4, 8, 12, 16 and 20 μM. The resultant mixtures in the respective cuvettes were individually allowed to react at 37° C. with respect to each of respective samples taken from the reaction mixtures in the six cuvettes, absorbances at 400 nm were measured 3 minutes and 5 minutes after the start of the reaction, and a change in absorbance as between the above two time points was calculated with respect to each of the samples. Results are shown in FIG. 5, which demonstrates the presence of good linearity in the relationship between the change (difference) in absorbance (with respect to the reaction mixture, as between 3 and 5 minutes after the start of the reaction) and the L-leucine concentration.

Example 6 Quantitative Determination of Pyruvic Acid

| | Reagent |
|---|---|
| 40 mM | triethanolamine hydrochloric acid-NaOH buffer (pH 8.5) |
| 4 mM | thio-NAD (manufactured by Sigma Co., Ltd., U.S.A.) |
| 0.1 mM | reduced NAD (Oriental Yeast Co., Ltd., Japan) |
| 50 mM | ammonium chloride (manufactured by Wako Pure Chemical Industries, Ltd., Japan) |
| 1250 u/ml | alanine dehydrogenase (EC 1.4;1.1) (derived from Sporolactobacillus sp. and manufactured by Asahi Chemical Industry Co., Ltd., Japan) |

Procedure 1 ml of the above reagent was placed in each of six test tubes. To the respective test tubes were individually added 20 μl each of six types of aqueous pyruvic acid solutions respectively having concentrations of 0, 50, 100, 150, 200 and 250 μM. The resultant mixtures in the respective test tubes were individually allowed to react at 37° C. 10

Figure 6:
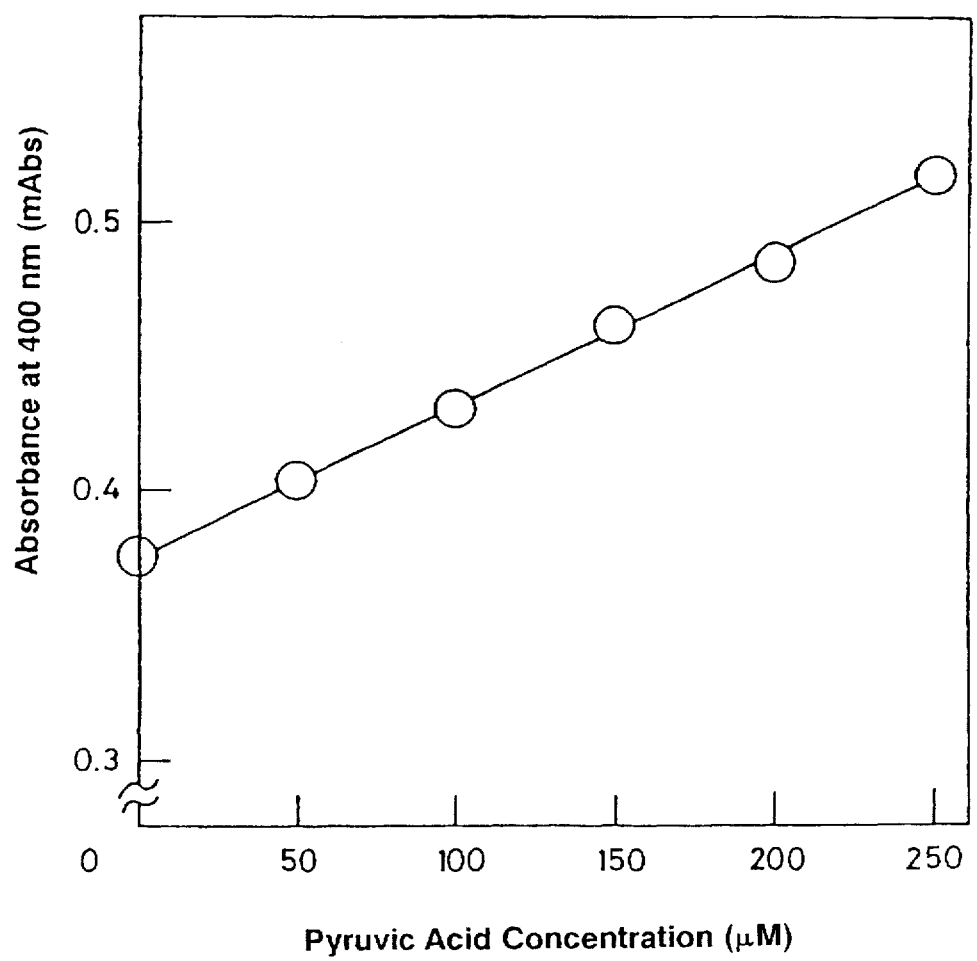
FIG. 6 is a graph showing the results of the rate assay of pyruvic acid at a wavelength of 400 nm conducted in Example 6.

Minutes after the start of the reaction, to each of the reaction mixtures in six test tubes was added 1 ml of an aqueous 2% sodium dodecyl sulfate (SDS) solution, to thereby terminate the reaction. After the termination of the reaction, absorbances at 400 nm were measured with respect to each of samples from the reaction mixtures in the six test tubes. Results are shown in FIG. 6, which demonstrates the presence of good linearity in the relationship between absorbance (with respect to the reaction mixture 10 minutes after the start of the reaction) and the pyruvic acid concentration.

Example 7 Quantitative Determination of Ammonia

| Reagent | |
|---|---|
| 40 mM | glycine-NaOH buffer (pH 10.0) |
| 3 mM | thio-NAD (manufactured by Sigma Co., Ltd., U.S.A.) |
| 50 mM | NADP (manufactured by Oriental Yeast Co., Ltd., Japan) |
| 8 mM | L-malic acid |
| 30 u/ml | malate dehydrogenase (EC 1.1.1.37) (derived from pig heart and manufactured by Boehringer Co., Ltd., Germany) |
| 3 mM | ADP (manufactured by Oriental Yeast Co., Ltd., Japan) |
| 5 mM | α-ketoglutaric acid (manufactured by Wako Pure Chemical Industries,. Ltd., Japan) |
| 3 mM | EDTA |
| 160 u/ml | glutamate dehydrogenase (derived from bovine liver and manufactured by Boehringer Co., Ltd., Germany) |

Figure 7:
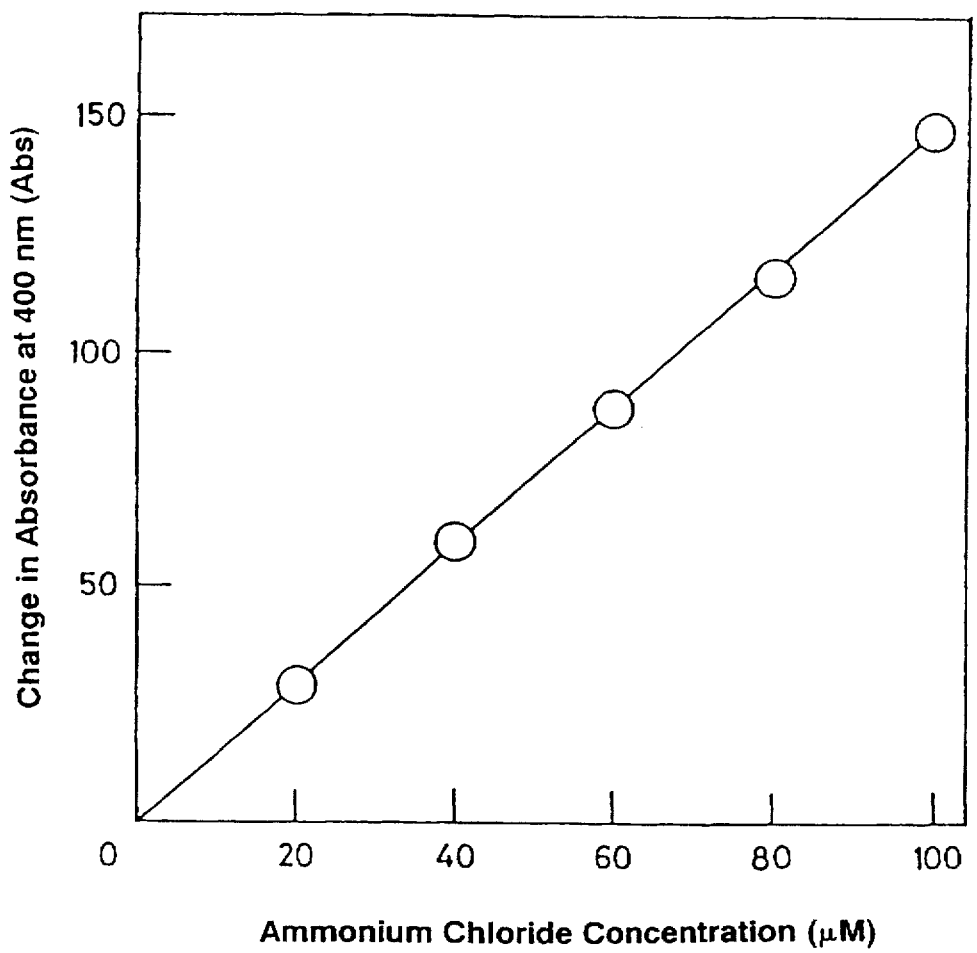
FIG. 7 is a graph showing the results of the rate assay of ammonium chloride at a wavelength of 400 nm conducted in Example 7.

Procedure 1 ml of the above reagent was placed in each of six cuvettes. To the respective cuvettes were individually added 50 μl each of six types of aqueous ammonium chloride solutions respectively having concentrations of 0, 20, 40, 60, 80 and 100 μM. The resultant mixtures in the respective cuvettes were individually allowed to react at 37° C. With respect to each of respective samples taken from the reaction mixtures in the six cuvettes, absorbances at 400 nm were measured 3 minutes and 8 minutes after the start of the reaction, and a change in absorbance as between the above two time points was calculated with respect to each of the samples. Results are shown in FIG. 7, which demonstrates the presence of good linearity in the relationship between the change (difference) in absorbance (with respect to the reaction mixture, as between 3 and 8 minutes after the start of the reaction) and the ammonium chloride concentration.

Example 8 Quantitative Determination of Ammonia

| Reagent | |
|---|---|
| 40 mM | Tris-HCl buffer (pH 8.0) |
| 0.25 mM | reduced NADP (manufactured by Oriental Yeast Co., Ltd., Japan) |
| 50 μM | thio-NAD (manufactured by Sigma Co., Ltd., U.S.A.) |
| 5 mM | dihydroxyaceton phosphate |
| 10 u/ml | glycerol-3-phosphate dehydrogenase (EC 1.1.1.8, derived from rabbit muscle and manufactured by Boehringer Co., Ltd., Germany) |
| 3 mM | ADP (manufactured by Oriental Yeast Co., Ltd., Japan) |
| 5 mM | α-ketoglutaric acid (manufactured by Wako Pure Chemical Industries, Ltd., Japan) |
| 3 mM | EDTA |
| 200 u/ml | glutamate dehydrogenase (derived from bovine liver and manufactured by Boehringer Co., Ltd., Germany) |

Figure 8:
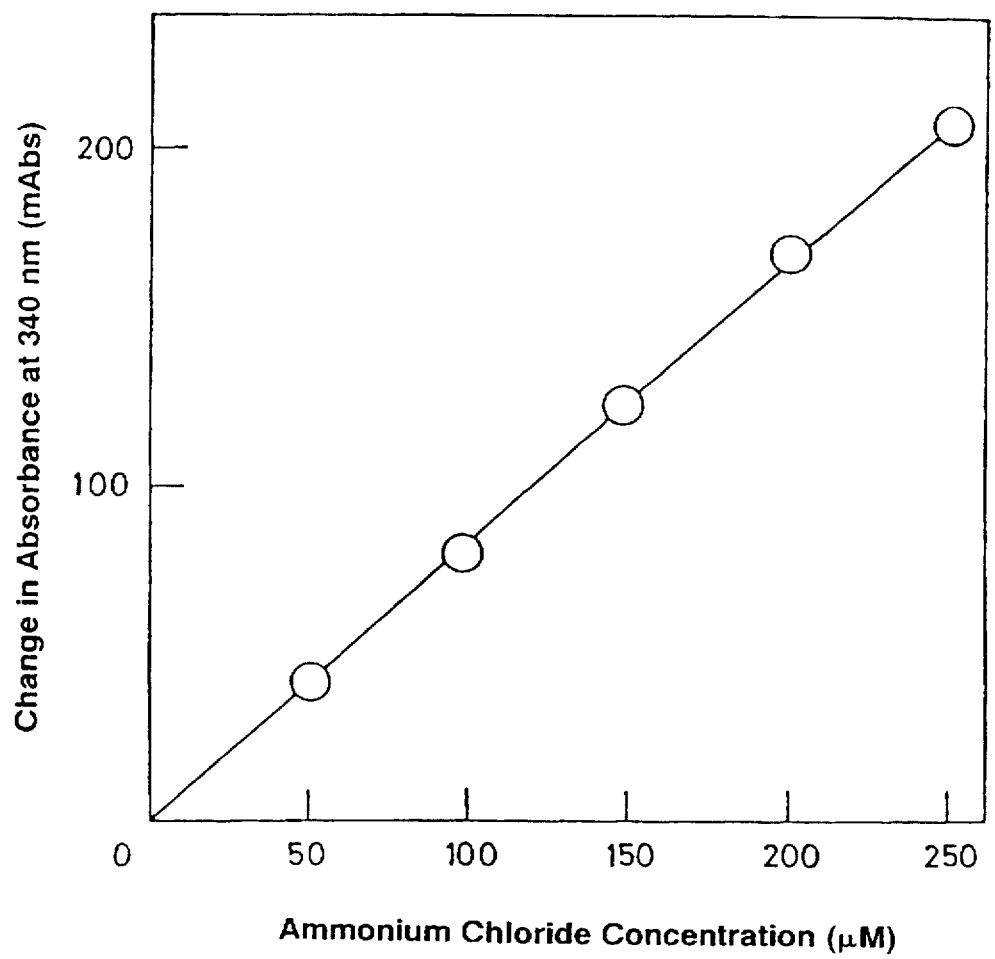
FIG. 8 is a graph showing the results of the rate assay of ammonium chloride at a wavelength of 340 nm conducted in Example 8.

Procedure 1 ml of the above reagent was placed in each of six cuvettes. To the respective cuvettes were individually added 50 μl each of six types of aqueous ammonium chloride solutions respectively having concentrations of 0, 50, 100, 150, 200 and 250 μM. The resultant mixtures in the respective cuvettes were individually allowed to react at 37° C. With respect to each of respective samples taken from the reaction mixtures in the six cuvettes, absorbances at 340 nm were measured 3 minutes and 8 minutes after the start of the reaction, and a change in absorbance as between the above two time points was calculated with respect to each of the samples. Results are shown in FIG. 8, which demonstrates the presence of good linearity in the relationship between the change (difference) in absorbance (with respect to the reaction mixture, as between 3 and 8 minutes after the start of the reaction) and the ammonium chloride concentration.

Industrial Applicability

According to the determination method of the present invention, an error in the quantitative determination of a target chemical substance can be minimized since two types of coenzymes exhibiting absorbances at different absorption wavelengths are used. Further, the sensitivity of the determination method can be greatly increased due to the utilization of the enzymatic cycling reaction. Thus, the method of the present invention ensures rapidness and accuracy in the determination of a target chemical substance, e.g., ammonia, an α-amino acid or an α-keto acid, even with the use of a small quantity of a biological sample. Therefore, the method of the present invention is very useful in application fields, such as clinical diagnosis and food testing.

We claim:

1. A method for the quantitative determination of a chemical substance selected from the group consisting of ammonia, an α-amino acid and an α-keto acid corresponding to said α-amino acid, which comprises:
   reacting a biological sample containing a target chemical substance selected from the group consisting of ammonia, an α-amino acid and an α-keto acid corresponding to said α-amino acid, with a reagent comprising:
   (1) an amino acid dehydrogenase which catalyzes the reversible reaction of an α-amino acid with water, said reaction producing ammonia and an α-keto acid corresponding to said α-amino acid, in the presence of (i) a first coenzyme selected from the group consisting of a thio-NADP compound and a thio-NAD compound and (ii) a second coenzyme selected from the group consisting of an NADP compound and an NAD compound,
   wherein said thio-NADP compound is selected from the group consisting of thionicotinamide adenine dinucleotide phosphate and thionicotinamide hypoxanthine dinucleotide phosphate, and said thio-NAD compound is selected from the group consisting of thionicotinamide adenine dinucleotide and thionicotinamide hyvoxanthine dinucleotide, and wherein said NADP compound is selected from the group consisting of nicotinamide adenine dinucleotide phosphate, acetylpyridine adenine dinucleotide phosphate, acetylpyridine hypoxanthine dinucleotide phosphate and nicotinamide hypoxanthine dinucleotide phosphate, and said NAD compound is selected from the group consisting of nicotinamide adenine dinucleotide, acetylpyridine adenine dinucleotide, acetylpyridine hypoxanthine dinucleotide and nicotinamide hypoxanthine dinucleotide;

(2) $A_1$; and (3) $B_1$; said components (1), (2) and (3) participating in the following cycling reaction (I):

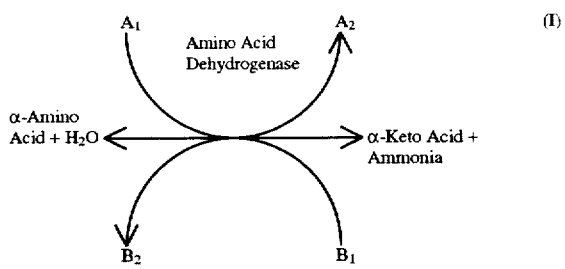

wherein $A_1$, is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$, with the proviso that when said target chemical substance is ammonia, said reagent further comprises an α-keto acid corresponding to the amino acid dehydrogenase as a nontarget chemical substance, and that when said target chemical substance is an α-keto acid, said reagent further comprises ammonia as a non-target chemical substance;

thereby effecting the cycling reaction (I);

measuring a change in absorbance at a wavelength specific for $A_2$ or $B_1$, which is caused for a predetermined period of time during said reaction (I); and correlating the measured change in absorbance of the target chemical substance with a calibration curve, which has been prepared from standard samples containing the target chemical substance in different concentrations, to quantify the amount of the target chemical substance.

2. The method according to claim 1, wherein said α-amino acid is L-glutamic acid, said α-keto Acid is α-ketoglutaric acid, and said amino acid dehydrogenase is glutamate dehydrogenase.

3. The method according to claim 1, wherein said α-amino acid is alanine, said α-keto acid is pyruvic acid, said amino acid dehydrogenase is alanine dehydrogenase, $A_1$ is a thio-NAD compound or an NAD compound, and $B_1$ is a reduced NAD compound when $A_1$ is a thio-NAD compound, or a reduced thio-NAD compound when $A_1$ is an NAD compound.

4. The method according to claim 1, wherein said α-amino acid is leucine, said α-keto acid is 2-oxoisocaproic acid, said amino acid dehydrogenase is leucine dehydrogenase, $A_1$ is a thio-NAD compound or an NAD compound, and $B_1$ is a reduced NAD compound when $A_1$ is a thio-NAD compound, or a reduced thio-NAD compound when $A_1$ is an NAD compound.

5. The method according to claim 1, wherein said target chemical substance is ammonia, said amino acid dehydrogenase (1) is selected from the group consisting of glutamate dehydrogenase, alanine dehydrogenase, leucine dehydrogenase, serine dehydrogenase, valine dehydrogenase, glycine dehydrogenase and L-amino acid dehydrogenase (EC 1.4.1.5), and said non-target chemical substance (4) is an α-keto acid corresponding to the α-amino acid which is used as a substrate for the selected amino acid dehydrogenase.

6. A method for the quantitative determination of a chemical substance selected from the group consisting of ammonia, an α-amino acid and an α-keto acid corresponding to said α-amino acid, which comprises:

reacting a biological sample containing a target chemical substance selected from the group consisting of ammonia, an α-amino acid and an α-keto acid corresponding to said α-amino acid, with a reagent comprising:

(1) an amino acid dehydrogenase as a first dehydrogenase which catalyzes the reversible reaction of an Δ-amino acid with water, said reaction producing ammonia and an Δ-keto acid corresponding to said Δ-amino acid, in the presence of (i) a first coenzyme selected from the group consisting of a thio-NADP compound and a thio-NAD compound and (ii) a second coenzyme selected from the group consisting of an NADP compound and an NAD compound, wherein said thio-NADP compound is selected from the group consisting of thionicotinamide adenine dinucleotide phosphate and thionicotinamide hypoxanthine dinucleotide phosphate, and said thio-NAD compound is selected from the group consisting of thionicotinamide adenine dinucleotide and thionicotinamide hypoxanthine dinucleotide, and wherein said NADP compound is selected from the group consisting of nicotinamide adenine dinucleotide phosphate, acetylpyridine adenine dinucleotide phosphate, acetylpyridine hypoxanthine dinucleotide phosphate and nicotinamide hypoxanthine dinucleotide phosphate, and said NAD compound is selected from the group consisting of nicotinamide adenine dinonucleotide, acetylpyridine adenine dinucleotide, acetylpyridine hypoxanthine dinucleotide and nicotinamide hypoxanthine dinucleotide;

(2) $A_1$;

(3) at least one coenzyme selected from $B_1$ and $B_2$; and (5) a second dehydrogenase which does not react with an Δ-amino acid but acts to advance the reaction for converting $B_2$ to $B_1$ in the following cycling reaction (ii), in combination with a substrate for said second dehydrogenase, said components (1), (2), (3) and (5) participating in the following cycling reaction (II):

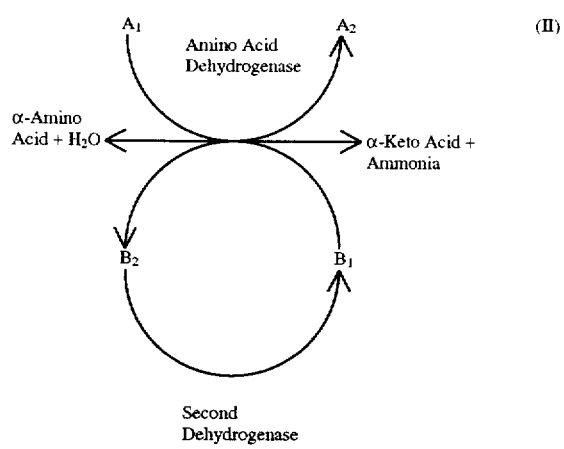

Second Dehydrogenase wherein $A_1$ is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$.

with the proviso that when said target chemical substance is ammonia, said reagent further comprises an Δ-keto acid corresponding to the amino acid dehydrogenase as a non-target chemical substance, and that when said target chemical substance is an Δ-keto acid, said reagent further comprises ammonia as a non-target chemical substance;

thereby effecting the cycling reaction (II); and measuring a change in absorbance at a wavelength specific for $A_2$, which is caused for a predetermined period of time during said reaction (II); and correlating the measured change in absorbance of the target chemical substance with a calibration curve, which has been prepared from standard samples containing the target chemical substance in different concentrations, to quantify the amount of the target chemical substance.

7. The method according to claim 6, wherein said α-amino acid is L-glutamic acid, said α-keto acid is α-ketoglutaric acid, and said amino acid dehydrogenase is glutamate dehydrogenase.

8. The method according to claim 6, wherein said α-amino acid is alanine, said α-keto acid is pyruvic acid, said amino acid dehydrogenase is alanine dehydrogenase, $A_1$ is a thio-NAD compound or an NAD compound, and $B_1$ is a reduced NAD compound when $A_1$ is a thio-NAD compound, or a reduced thio-NAD compound when $A_1$ is an NAD compound.

9. The method according to claim 6, wherein said α-amino acid is leucine, said α-keto acid is 2-oxoisocaproic acid, said amino acid dehydrogenase is leucine dehydrogenase, $A_1$ is a thio-NAD compound or an NAD compound, and $B_1$ is a reduced NAD compound when $A_1$ is a thio-NAD compound, or a reduced thio-NAD compound when $A_1$ is an NAD compound.

10. The method according to claim 6, wherein said target chemical substance is ammonia, said amino acid dehydrogenase (1) is selected from the group consisting of glutamate dehydrogenase, alanine dehydrogenase, leucine dehydrogenase, serine dehydrogenase, valine dehydrogenase, glycine dehydrogenase and a common amino acid dehydrogenase, and said non-target chemical substance (4) is an α-keto acid corresponding to the α-amino acid which is used as a substrate for the selected amino acid dehydrogenase.

11. A method for the quantitative determination of a chemical substance selected from the group consisting of ammonia, an α-amino acid and an α-keto acid corresponding to said α-amino acid, which comprises:

reacting a biological sample containing a target chemical substance selected from the group consisting of ammonia, an α-amino acid and an α-keto acid corresponding to said α-amino acid, with a reagent comprising:

(1) an amino acid dehydrogenase as a first dehydrogenase which catalyzes the reversible reaction of an α-amino acid with water, said reaction producing ammonia and an α-keto acid corresponding to said α-amino acid, in the presence of (i) a first coenzyme selected from a thio-NADP compound and a thio-NAD compound and (ii) a second coenzyme selected from the group consisting of an NADP compound and an NAD compound, wherein said thio-NADP compound is selected from the group consisting of thionicotinamide adenine dinucleotide phosphate and thionicotinamide hypoxanthine dinucleotide phosphate, and said thio-NAD compound is selected from the group consisting of thionicotinamide adenine dinucleotide and thionicotinamide hypoxanthine dinucleotide, and wherein said NADP compound is selected from the group consisting of nicotinamide adenine dinucleotide phosphate, acetylpyridine adenine dinucleotide phosphate, acetylpyridine hypoxanthine dinucleotide phosphate and nicotinamide hypoxanthine dinucleotide phosphate, and said NAD compound is selected from the consisting of nicotinamide adenine dinucleotide, acetylpyridine adenine dinucleotide, acetylpyridine hypoxanthine dinucleotide and nicotinamide hypoxanthine dinucleotide;

(2) at least one coenzyme selected from $A_1$ or $A_2$;

(3) $B_1$; and (6) a third dehydrogenase which does not react with an α-amino acid but acts to advance the reaction for converting $A_2$ to $A_1$ in the following cycling reaction (III), in combination with a substrate for said third dehydrogenase, said components (1), (2), (3) and (6) participating in the following cycling reaction (III):

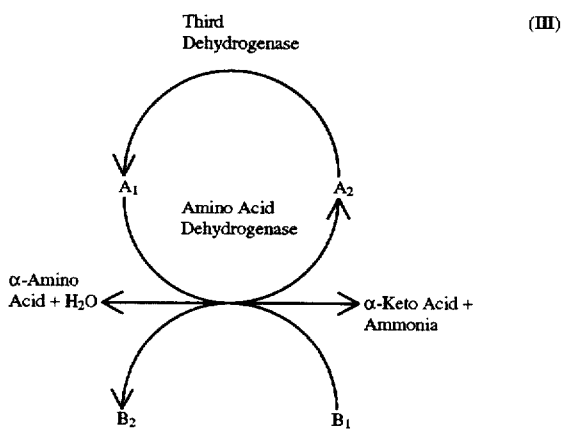

wherein $A_1$ is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$, with the proviso that when said target chemical substance is ammonia, said reagent further comprises an α-keto acid corresponding to the amino acid dehydrogenase as a non-target chemical substance, and that when said target chemical substance is an α-keto acid, said reagent further comprises ammonia as a non-target chemical substance;

thereby effecting the cycling reaction (III); measuring a change in absorbance at a wave-length specific for $B_1$, which is caused for a predetermined period of time during said reaction; and correlating the measured change in absorbance of the target chemical substance with a calibration curve, which has been prepared from standard samples containing the target chemical substance in different concentrations, to quantify the amount of the target chemical substance.

12. The method according to claim 11, wherein said α-amino acid is L-glutamic acid, said α-keto acid is α-ketoglutaric acid, and said amino acid dehydrogenase is glutamate dehydrogenase.

13. The method according to claim 11, wherein said α-amino acid is alanine, said α-keto acid is pyruvic acid, said amino acid dehydrogenase is alanine dehydrogenase, $A_1$ is a thio-NAD compound or an NAD compound, and $B_1$ is a reduced NAD compound when $A_1$ is a thio-NAD compound, or a reduced thio-NAD compound when $A_1$ is an NAD compound.

14. The method according to claim 11, wherein said α-amino acid is leucine, said α-keto acid is 2-oxoisocaproic acid, said amino acid dehydrogenase is leucine dehydrogenase, $A_1$ is a thio-NAD compound or an NAD compound, and $B_1$ is a reduced NAD compound when $A_1$ is a thio-NAD compound, or a reduced thio-NAD compound when $A_1$ is an NAD compound.

15. The method according to claim 11, wherein said target chemical substance is ammonia, said amino acid dehydrogenase (1) is selected from the group consisting of glutamate dehydrogenase, alanine dehydrogenase, leucine dehydrogenase, serine dehydrogenase, valine dehydrogenase, glycine dehydrogenase and a common amino acid dehydrogenase, and said non-target chemical substance (4) is an α-keto acid correspo nding to the α-amino acid which is used as a substrate for the selected amino acid dehydrogenase.

16. An analytical composition for the quantitative determination of a chemical substance selected from the group consisting of ammonia, an α-amino acid and an α-keto acid corresponding to said α-amino acid, which comprises:

(1) an amino acid dehydrogenase as a first dehydrogenase which catalyzes the reversible reaction of an α-amino acid with water, said reaction producing ammonia and an α-keto acid corresponding to said α-amino acid, in the presence of (i) a first coenzyme selected from the group consisting of a thio-NADP compound and a thio-NAD compound and (ii) a second coenzyme selected from the group consisting of an NADP compound and an NAD compound, wherein said thio-NADP compound is selected from the group consisting of thionicotinamide adenine dinucleotide phosphate and thionicotinamide hypoxanthine dinucleotide phosphate, and said thio-NAD compound is selected from the group consisting of thionicotinamide adenine dinucleotide and thionicotinamide hyroxanthine dinucleotide, and wherein said NADP compound is selected from the group consisting of nicotinamide adenine dinucleotide phosphate, acetylpyridine adenine dinucleotide phosphate, acetylpyridine hypoxanthine adenine dinucleotide phosphate, acetylpyridine hypoxanthine dinucleotide phosphate and nicotinamide hypoxanthine dinucleotide phosphate, and said NAD compound is selected from the group consisting of nicotinamide adenine dinucleotide, acetylpyridine adenine dinucleotide, acetylpryridine hypoxanthine dinucleotide and nicotinamide hypoxanthine dinucleotide;

(2) $A_1$; and (3) $B_1$; said components (1), (2) and (3) participating in the following cycling reaction (I):

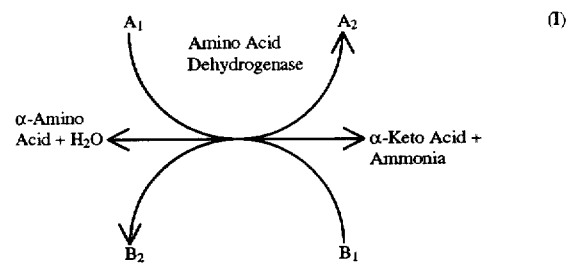

wherein $A_1$ is a thio-NADP compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$, with the proviso that when said target chemical substance is ammonia, said reagent further comprises an α-keto acid corresponding to the amino acid dehydrogenase as a non-target chemical substance, and that when said target chemical substance is an α-keto acid, said reagent further comprises ammonia as a non-target chemical substance.

17. An analytical composition for the quantitative determination of a chemical substance selected from the group consisting of ammonia, an α-amino acid and an α-keto acid corresponding to said α-amino acid, which comprises:

(1) an amino acid dehydrogenase as a first dehydrogenase which catalyzes the reversible reaction of an α-amino acid with water, said reaction producing ammonia and an α-keto acid corresponding to said α-amino acid, in the presence of (i) a first coenzyme selected from the group consisting of a thio-NADP compound and a thio-NAD compound and (ii) a second coenzyme selected from the group consisting of an NADP compound and an NAD compound, wherein said thio-NADP compound is selected from the group consisting of thionicotinamide adenine dinucleotide phosphate and thionicotinamide hypoxanthine dinucleotide phosphate, and said thio-NAD compound is selected from the group consisting of thionicotinamide adenine dinucleotide and thionicotinamide hypoxanthine dinucleotide, and wherein said NADP compound is selected from the group consisting of nicotinamide adenine dinucleotide phosphate, acetylpyridine adenine dinucleotide phosphate, acetyloyridine hypoxanthine dinucleotide phosphate and nicotinamide hypoxanthine dinucleotide phosphate, and said NAD compound is selected from the group consisting of nicotinamide adenine dinucleotide, acetylryridine adenine dinucleotide, acetylryridine hypoxanthine dinucleotide and nicotinamide hypoxanthine dinucleotide;

(2) $A_1$;

(3) at least one coenzyme selected from $B_1$ and $B_2$; and (5) a second dehydrogenase which does not react with an α-amino acid but acts to advance the reaction for converting $B_2$ to $B_1$ in the following cycling reaction (II), in combination with a substrate for said second dehydrogenase, said components (1), (2), (3) and (5) participating in the following cycling reaction (II):

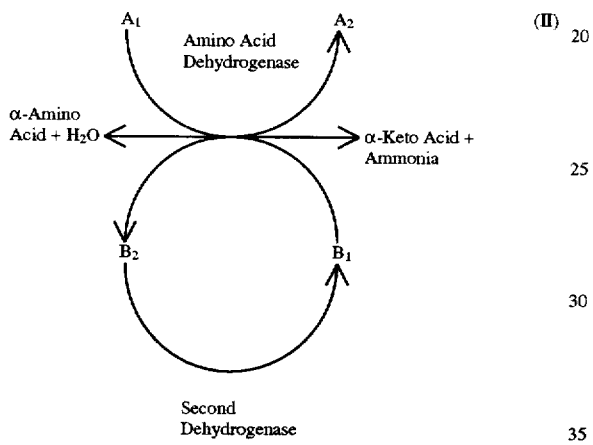

wherein $A_1$ is a thio-NADP compound, a thio-NAD compound, an NADP compound or an NAD compound; $A_2$ is a reduced product of $A_1$; $B_1$ is a reduced NADP Compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized product of $B_1$, with the proviso that when said target chemical substance is ammonia, said reagent further comprises an α-keto acid corresponding to the amino acid dehydrogenase as a non-target chemical substance, and that when said target chemical substance is an α-keto acid, said reagent further comprises ammonia as a non-target chemical substance.

18. An analytical composition for the quantitative determination of a chemical substance selected from the group consisting of ammonia, an α-amino acid and an α-keto acid corresponding to said α-amino acid, which comprises:

(1) an amino acid dehydrogenase as a first dehydrogenase which catalyzes the reversible reaction of an α-amino acid with water, said reaction producing ammonia and an α-keto acid corresponding to said α-amino acid, in the presence of (i) a first coenzyme selected from the group consisting of a thio-NADP compound and a thio-NAD compound and (ii) a second coenzyme selected from the group consisting of an NADP compound and an NAD compound, wherein said thio-NADP compound is selected from the group consisting of thionicotinamide adenine dinucleotide phosphate and thionicotinamide hypoxanthine dinucleotide phosphate, and said thio-NAD compound is selected from the group consisting of thionicotinamide adenine dinucleotide and thionicotinamide hypoxanthine dinucleotide, and wherein said NADP compound is selected from the group consisting of nicotinamide adenine dinucleotide phosphate, acetylpyridine adenine dinucleotide phosphate, acetylpyridine hypoxanthine dinucleotide phosphate and nicotinamide hypoxanthine dinucleotide phosphate, and said NAD compound is selected from the group consisting of nicotinamide adenine dinucleotide, acetylpyridine adenine dinucleotide, acetylpyridine hypoxanthine dinucleotide and nicotinamide hypoxanthine dinucleotide;

(2) at least one coenzyme selected from $A_1$ and $A_2$;

(3) $B_1$; and (6) a third dehydrogenase which does not react with an α-amino acid but acts to advance the reaction for converting $A_2$ to $A_1$ in the following cycling reaction (III), in combination with a substrate for said third dehydrogenase, said components (1), (2), (3) and (6) participating in the following cycling reaction (III):

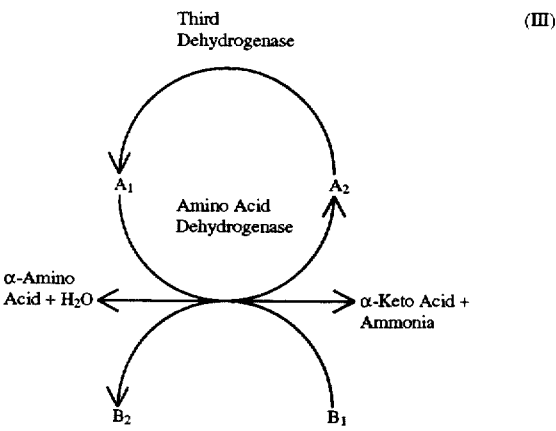

wherein $A_1$ is a thio-NADP Compound, a thio-NAD compound, an NADP compound or an NAD compound; $A_2$ is a reduced product of $A_1$; $B_1$ is a reduced NADP compound or a reduced NAD compound when $A_1$ is a thio-NADP compound or a thio-NAD compound, or a reduced thio-NADP compound or a reduced thio-NAD, compound when $A_1$ is an NADP compound or an NAD compound; and $B_2$ is an oxidized product of $B_1$, with the proviso that when said target chemical substance is ammonia, said reagent further comprises an α-keto acid corresponding to the amino acid dehydrogenase as a non-target chemical substance, and that when said target chemical substance is an α-keto acid, said reagent further comprises ammonia as a non-target chemical substance.

* * * * *

UNITED STATES PATENT AND TRADEMARK OFFICE
CERTIFICATE OF CORRECTION

PATENT NO. : 5,780,256
DATED : July 14, 1998
INVENTOR(S) : UEDA, et al

It is certified that error appears in the above-identified patent and that said Letters Patent is hereby corrected as shown below:

On cover page, item [54], "$\alpha$" should be changed to --ALPHA--.

In column 1, line 3, "$\alpha$" should be changed to --ALPHA--.

In column 18, line 66, "hyvoxanthine" should be changed to --hypoxanthine--.

In column 19, line 9, "dinucleotide:" should be changed to --dinucleotide;--.

In column 19, line 23, "$A_1$," should be changed to --$A_1$--.

In column 19, line 37, "substance:" should be changed to --substance--.

In column 20, lines 28, 29, 30 and 55, "$\Delta$" should be changed to --$\alpha$--.

In column 20, line 57, "(ii)" should be changed to --(III)--.

In column 21, lines 28 and 31, "$\Delta$" should be changed to --$\alpha$--.

In column 22, line 36, "the consisting" should be changed to --the group consisting--.

In column 23, line 10, "substance." should be changed to --substance,--

In column 23, line 50, "correspo nding" should be changed to --corresponding--.

In column 24, lines 4-5, "hyroxanthine" should be changed to --hypoxanthine--.

In column 25, line 38-39, "Compound" should be changed to --compound--.

UNITED STATES PATENT AND TRADEMARK OFFICE
CERTIFICATE OF CORRECTION

PATENT NO. : 5,780,256
DATED : July 14, 1998
INVENTOR(S) : UEDA, et al

It is certified that error appears in the above-identified patent and that said Letters Patent is hereby corrected as shown below:

In column 26, lines 47, "Compound" should be changed to --compound--.

In column 26, line 52, "thio-NAD," should be changed to --thio-NAD--.

Signed and Sealed this

Twenty-eighth Day of March, 2000

Attest:

Q. TODD DICKINSON

Attesting Officer

Commissioner of Patents and Trademarks